United States Patent
Kratz et al.

(10) Patent No.: US 7,141,691 B2
(45) Date of Patent: Nov. 28, 2006

(54) PROTEIN-BOUND DERIVATIVES OF PLATINUM COMPLEXES CONTAINING CYCLOBUTANE1, 1-DICARBOXYLLATE LIGANDS

(75) Inventors: Felix Kratz, Ihringen (DE); André Warnecke, Freiburg (DE)

(73) Assignee: KTB Tumorforschungs GmbH, Freiburg (DE)

( * ) Notice: Subject to any disclaimer, the term of this patent is extended or adjusted under 35 U.S.C. 154(b) by 0 days.

(21) Appl. No.: 10/549,311

(22) PCT Filed: Mar. 18, 2004

(86) PCT No.: PCT/EP2004/002850

§ 371 (c)(1),
(2), (4) Date: Sep. 16, 2005

(87) PCT Pub. No.: WO2004/083223

PCT Pub. Date: Sep. 30, 2004

(65) Prior Publication Data

US 2006/0089341 A1    Apr. 27, 2006

(30) Foreign Application Priority Data

Mar. 19, 2003  (DE) ................ 103 14 780

(51) Int. Cl.
*C07F 15/00* (2006.01)
*A61K 31/28* (2006.01)
(52) U.S. Cl. ............ 556/137; 556/136; 514/492
(58) Field of Classification Search ............ 556/136, 556/137; 514/492
See application file for complete search history.

(56) References Cited

U.S. PATENT DOCUMENTS 5,011,959 A * 4/1991 Khokhar et al. ......... 556/137
7,038,071 B1 * 5/2006 Lal ....................... 556/136

* cited by examiner

*Primary Examiner*—Porfirio Nazario-Gonzalez
(74) *Attorney, Agent, or Firm*—Millen, White, Zelano & Branigan (57) ABSTRACT

The invention concerns low-molecular platinum complexes containing cyclobutane-1,1-dicarboxylate ligands that contain a protein-binding group.

15 Claims, 1 Drawing Sheet

Figure 1

PROTEIN-BOUND DERIVATIVES OF PLATINUM COMPLEXES CONTAINING CYCLOBUTANE1, 1-DICARBOXYLLATE LIGANDS

The invention concerns low-molecular platinum complexes of cyclobutane-1,1-dicarboxylate ligands which contain a protein-binding group, their production and use.

Carboplatin (diammine platinum(II)-cyclobutane-1,1-dicarboxylate) is an anti-neoplastic platinum(II) complex that is used to treat various cancer diseases (Woloschuk, D. M. et al., *Drug Intell. Clin. Pharm.* 1988, 22, 843–849). Carboplatin differs from the structurally related cisplatin (cis-diammine dichloroplatinum(II)) in that the chloroligands are replaced by a chelating cyclobutane-1,1-dicarboxylate ligand wherein changes in pharmacokinetics result as well as in a toxicity profile that is different from cisplatin (Lokich, J., *Cancer Invest.* 2001, 19, 756–760). However, therapies with carboplatin is accompanied by side-effects (Go, R. S. et al., *J. Clin. Oncol.* 1999, 17, 409–422). In order to improve the side-effect profile and the efficacy of cytostatic agents, it has already been proposed that protein-binding formulations should be developed which couple in vivo to endogenous serum proteins and in this manner represent macromolecular transport forms of the active substances (Kratz, F. et al., *Am. Assoc. Cancer Res.* 2001, 42, 138–139, Kratz, F. et al., *J. Med. Chem.* 2000, 43, 1253–1256).

The object of the invention is to create protein-binding derivatives of carboplatin which have fewer undesired side-effects and a higher efficacy towards tumor tissue.

This object is achieved according to the invention by low-molecular carboplatin derivatives of the general formula I (I)

in which R=2H,

—(CH$_2$)$_i$— (i=2 or 3), X=O or NH, Y=O, S or 2H, n=0 to 5, m=0 to 6 and PM is a protein-binding group.

The compounds according to the invention are composed of an anti-tumoral cis-configured platinum(II) complex and a heterobifunctional cross-linker. This structure is elucidated in more detail in the following:

The anti-tumoral platinum complex is a derivative of an active substance having the general formula II (II)

in which

R=2H, —(CH$_2$)$_i$— (i=2 or 3) X=OH or NH$_2$. It differs from the clinical standard carboplatin in that a hydroxy or amino group is present on the cyclobutane ring and optionally in that chelating amine ligands such as trans-1,2-diaminocyclohexane, cis-1,2-diaminocyclohexane, ethylene diamine or 1,3-diaminopropane are present.

The heterobifunctional cross-linker is a carboxylic acid derivative or an alcohol containing a protein-binding group of the general formula III

(III)

in which
Y=2H, O or S
n=0 to 5
m=0 to 6
PM=a protein-binding group.

The protein-binding group (PM) is preferably selected from a 2-dithiopyridyl group, a halogen acetamide group, a halogen acetate group, a disulfide group, an acrylic acid ester group, a monoalkylmaleic acid ester group, a monoalkylmaleaminic acid amide group, an N-hydroxysuccinimidyl ester group, an isothiocyanate group, an aziridine group or a maleinimide group. The maleinimide group is a particularly preferred protein-binding group.

Compounds according to the invention are obtained formally by condensing the active substance derivative with the cross-linker. Hence there is an ester bond, an amide bond, a thioester bond, a thioamide bond, an ether bond or an amine bond between the active substance derivative and the cross-linker.

The platinum complexes according to the invention are preferably prepared by reacting a cyclobutane-1,1-dicarboxylic acid derivative of the general formula IV (IV)

in which

X=O or NH

Y=O, S or 2H m=0 to 5 n=0 to 6 and PM denotes a protein-binding group, with a platinum complex of the general formula V (V)

in which R=2H,

—$(CH_2)_i$— (i=2 or 3) R'=$2NO_2$, $SO_2$ or CO.

For the reaction the platinum complex can for example be dissolved in water and admixed with the cyclobutane-1,1-dicarboxylic acid derivative or an alkali or alkaline earth metal salt of the cyclobutane-1,1-dicarboxylic acid derivative. The reactions are expediently carried out at temperatures between 0° C. and 50° C. in which case the reaction time is normally between 1 and 24 hours. The product can be isolated by common methods such as crystallization, chromatography on silica gel or reversed phase chromatography (preparative HPLC).

According to a preferred embodiment, an aqueous solution of a cis-diaminoalkyl platinum(II) dinitrate complex or cis-diammine platinum(II) dinitrate is reacted with a cyclobutane-1,1-dicarboxylic acid derivative which has a maleinimide group and an oligo(ethylene glycol) backbone at a pH between 5 and 6. The platinum complexes obtained in this manner are preferably purified by column chromatography on silica gel or by reversed phase chromatography (see examples 5, 6 and 9). Platinum complexes obtained in this manner have an excellent water-solubility.

The cyclobutane-1,1-dicarboxylic acid derivatives having a maleinimide group and an oligo(ethylene glycol) backbone that are preferably used for the complex formation can be prepared in a four-step synthesis starting with bis(4-methoxy-benzyl)malonate and 1,3-dibromo-2-tert.-butyldimethylsiloxypropane:

In the first step bis(4-methoxybenzyl)malonate is dialkylated with 1,3-dibromo-2-tert.-butylsiloxypropane which results in a cyclobutane ring system.

This reaction is preferably carried out in an aprotic polar solvent such as dioxane or DMF using bases such as potassium hydride, sodium hydride or sodium hexamethyldisilazide at temperatures of >100° C. Under these conditions the reaction time is typically 48–120 hours (see example 1).

In the second step the tert.-butyldimethylsilyl protecting group is cleaved by methods that are familiar to a person skilled in the art preferably using tetrabutyl-ammonium fluoride in tetrahydrofuran (see example 2).

In the third step the 3-hydroxy group of the cyclobutane ring of bis(4-methoxybenzyl)-3-hydroxycyclobutane-1,1-dicarboxylate is esterified with a maleinimidocarboxylic acid of the general formula VIa.

(VIa)

in which
n=0 to 5
m=0 to 6.

In this step the reagents that are preferably used to activate the carboxyl group of the cross-linker are N,N'-dicyclohexylcarbodiimide, N,N'-diisopropylcarbodiimide, (benzotriazol-1-yloxy)tris(dimethylamino)phosphonium hexafluorophosphate or 2-chloro-1-methylpyridinium iodide with addition of conventional catalysts or auxiliary bases such as trialkylamines, pyridine, 4-dimethylaminopyridine (DMAP) or hydroxybenzotriazole (HOBt). The reaction is expediently carried out in a polar organic solvent, preferably in dichloromethane, N,N-dimethylformamide and tetrahydrofuran. The reactions are expediently carried out at temperatures between −10° C. to room temperature, in which case the reaction period is normally between 3 and 48 hours.

According to a preferred embodiment bis(4-methoxybenzyl)-3-hydroxycyclo-butane-1,1-dicarboxylate is reacted with a maleinimidocarboxylic acid which has an oligo (ethylene glycol) backbone, using 2-chloro-1-methylpyridinium iodide (see examples 3 and 7) to form a compound of the general formula VII.

In the fourth step the 4-methoxybenzyl protecting group is cleaved off with trifluoroacetic acid and anisole at 0° C. (see examples 4 and 8).

(VII)

THF, anisole | CH$_2$Cl$_2$

-continued

An important feature of the platinum complexes according to the invention is that they bind rapidly and covalently to serum proteins via the protein-binding group which generates a macromolecular transport form of the active substance. It is known that serum proteins such as transferrin, albumin and LDL have a higher uptake into tumor tissue (Kratz F.; Beyer U. Drug *Delivery* 1998, 5, 281–299) so that they can be used within the scope of the invention as endogenous carriers for cytostatic agents. Circulating human serum albumin (HSA) which is the main protein component of human blood having an average concentration of 30 to 50 g/l (Peters T. *Adv. Protein Chem.* 1985, 37, 161–245) and has a free cysteine group (cysteine 34 group) on the surface of the protein that is suitable for binding thiol-binding groups such as maleinimides or disulfides (WO 00/76551), is a particularly preferred serum protein.

The protein-binding platinum complexes according to the invention can be administered as drugs either parenterally or preferably intravenously. For this purpose the platinum complexes according to the invention are provided as solutions, solids or lyophilisates, optionally using standard auxiliary agents. Such auxiliary agents are for example polysorbates, glucose, lactose, mannitol, dextrans, citric acid, tromethamol, triethanolamine, aminoacetic acid and/or synthetic polymers. The administered complexes then react with serum proteins to form the transport form.

The new platinum complexes can also be reacted extracorporeally with serum proteins e.g. with an amount of albumin, blood or serum provided for infusion.

Protein-bound platinum complexes according to the invention have different pharmacokinetics compared to conventional low-molecular complexes and accumulate in tumor tissue due to their macromolecular character. The cyclobutane-1,1-dicarboxylate ligand that is bound in a labile manner is cleaved by an intracellular hydrolytic reaction which releases aquo, hydroxy or mixed aquohydroxy complexes as active components. In experimental studies on animals these protein-binding platinum complexes were more effective than the clinical standard carboplatin (see example 10).

The invention is elucidated in more detail by the following examples in conjunction with the figures. The figure shows a graph of the results of an animal experiment with a substance according to the invention compared to carboplatin on the basis of a change in the tumor volume.

EXAMPLE 1

Preparation of bis(4-methoxybenzyl)-3-tert.-butyldimethyl-siloxycyclobutane-1,1-dicarboxylate (PMB-CB-OTBS)

Bis(4-methoxybenzyl)malonate (6.00 g, 17.4 mmol) is added dropwise within 30 minutes to a suspension of potassium hydride (35% in mineral oil) (2.10 g, 18.29 mmol) in 20 ml anhydrous dioxane under an inert gas atmosphere. It is allowed to stir for a further 15 min at room temperature. 1,3-dibromo-2-tert.-butyldimethylsiloxypropane (6.08 g, 18.29 mmol) is added and it is heated overnight under reflux. Potassium hydride (35% in mineral oil) (2.10 g, 18.29 mmol) is slowly added as a suspension in 10 ml dioxane to the reaction mixture which is cooled to room temperature. It is subsequently stirred for three further days under reflux. The potassium bromide that forms is filtered over Celite, the solvent is removed in a vacuum and the residue is purified by column chromatography (silica gel, ethyl acetate/isohexane 1:10). 2.78 g PBM-CB-OTBS (31% of theory) is obtained as a colourless oil.

EXAMPLE 2

Preparation of bis(4-methoxybenzyl)-3-hydroxycyclobutane-1,1-dicarboxylate (PMB-CB-OH)

A solution of PMB-CB-OTBS (2.69 g, 5.23 mmol) in 25 ml anhydrous THF is admixed with tetrabutylammonium fluoride (2.47 g, 7.85 mmol) and stirred for 15 min at room temperature. Subsequently the solvent is removed in a vacuum and the residue is purified by column chromatography (silica gel, ethyl acetate/isohexane 1:1). 1.85 g PMB-CB-OH (88% of theory) is obtained as a colourless oil which slowly crystallizes.

EXAMPLE 3

Preparation of bis(4-methoxybenzyl)-3-(6-maleinimido-4-oxacaproyl)cyclobutane-1,1-dicarboxylate (PMB-CB-1-Mal)

A solution of PMB-CB-OH (1.97 g, 4.91 mmol), 6-maleinimido-4-oxacaproic acid (1.57 g, 7.37 mmol) and triethylamine (2.04 ml, 8.64 mmol) is admixed with 2-chloro-1-methylpyridinium iodide (1.88 g, 7.37 mmol) in 30 ml anhydrous dichloromethane and stirred for three hours at room temperature. It is diluted with 140 ml dichloromethane, washed each time twice with 80 ml in hydrochloric acid, 80 ml water and once each time with 80 ml sodium chloride solution (saturated) and dried over magnesium sulfate. Subsequently the solvent is removed in a vacuum and the residue is purified by column chromatography (silica gel, chloroform/methanol 200:1). 2.89 g PMB-CB-1-Mal (99% of theory) is obtained as a colourless oil.

EXAMPLE 4

Preparation of 3-(6-maleinimido-4-oxacaproyl)cyclobutane-1,1-dicarboxylic acid (COOH-CB-1-Mal)

A solution of PMB-CB-1-Mal (2.76 g, 4.63 mmol) and anisole (7.57 ml, 69.5 mmol) is admixed with 10 ml trifluoroacetic acid in 50 ml anhydrous dichloromethane at 0° C. and stirred for two hours at 0° C. Subsequently the solvent is removed in a vacuum and the residue is purified by column chromatography (silica gel, chloroform/methanol 20:1). 1.28 g COOH-CB-1-Mal (78% of theory) is obtained as a colourless syrup.

EXAMPLE 5

Preparation of trans-(R,R/S,S)-cyclohexane-1,2-diaminoplatinum(II)-[3-(6-maleinimido-4-oxacaproyl)cyclobutane-1,1-dicarboxylate](DACH-Pt-CB-1-Mal)

A solution of COOH-CB-1-Mal (271 mg, 762 µmol) in 5 ml water is added to an aqueous solution of [Pt trans-DACH](NO$_3$)$_2$ (300 mg, 692 µmol) which is cooled to room temperature, the latter being obtained by heating (50° C.) the platinum complex with 60 ml water. The reaction mixture is adjusted to pH 5.5 with 0.1 M KOH and stirred for three hours at room temperature in the dark. Subsequently the solvent is removed in a vacuum and the residue is purified by column chromatography (silica gel, ethanol). 291 mg DACH-Pt-CB-1-Mal (61% of theory) is obtained as a colourless solid.

¹H-NMR (CD₃OD): δ=0.97–1.29 (m, 4H, cyclohexyl-$\underline{H}$), 1.38–1.56 (m, 2H, cyclohexyl-$\underline{H}$), 1.81–1.96 (m, 2H, cyclohexyl-$\underline{H}$), 2.19–2.36 (m, 2H, cyclohexyl-$\underline{H}$), 2.42 (t, J=5.9 Hz, C$\underline{H}_2$COO), 2.60–2.79 (m, 2H, C$\underline{H}_2$CHOR), 3.27–3.41 (m, 2H, C$\underline{H}_2$CHOR), 3.46–3.66 (m, 6H, NC$\underline{H}_2$, OC$\underline{H}_2$), 4.67–4.86 (m, 1H, C$\underline{H}$OR), 6.76 (s, 2H, C(O)C$\underline{H}$=C$\underline{H}$CO)

¹³C-NMR (CD₃OD): δ=25.51, 33.30 (cyclohexyl), 35.92 ($\underline{C}$H₂COO), 38.17 (N$\underline{C}$H₂), 39.80/40.09 ($\underline{C}$H₂CHOR), 51.35 ($\underline{C}$(COOH)₂), 63.81/63.86 (cyclohexyl-NH₂), 65.66 ($\underline{C}$HOR), 67.22, 68.65 (O$\underline{C}$H₂), 135.50 (C(O)$\underline{C}$H=$\underline{C}$HCO), 172.52, 172.80 ($\underline{C}$(O)CH=CH$\underline{C}$O, CH₂$\underline{C}$OO), 180.41, 180.61 (C($\underline{C}$OOH)₂)

ESI-MS (4.0 kV, MeOH):

m/z (%) 663.0 ([M+1]⁺, 100)

EXAMPLE 6

Preparation of diammine platinum(II)-[3-(6-maleinimido-4-oxacaproyl)cyclobutane-1,1-dicarboxylate] ((NH₃)₂-Pt-CB-1-Mal)

A solution of COOH-CB-1-Mal (538 mg, 1.51 mmol) in 5 ml water is added to an aqueous solution of [(NH₃)₂Pt](NO₃)₂ (485 mg, 1.37 mmol) which is cooled to room temperature, the latter being obtained by heating (50° C.) the platinum complex with 90 ml water. The reaction mixture is adjusted to pH 5.5. with 0.1 M KOH and stirred for three hours at room temperature in the dark. Subsequently the solvent is removed in a vacuum and the residue is purified by column chromatography (silica gel, ethanol). 263 mg (NH₃)₂-Pt-CB-1-Mal (33% of theory) is obtained as a colourless solid.

ESI-MS:

m/z (%) 581.8 ([M]⁺, 100)

EXAMPLE 7

Preparation of bis(4-methoxybenzyl)-3-(15-maleinimido-4,7,10,13-tetroxapentadecanoyl)cyclobutane-1,1-dicarboxylate (PMB-CB-4-Mal)

A solution of PMB-CB-OH (1.154 g, 2.881 mmol), 15-maleinimido-4,7,10,13-tetroxapentadecanoic acid (1.49 g, 4.32 mmol) and triethylamine (1.20 ml, 8.64 mmol) in 20 ml anhydrous dichloromethane is admixed with 2-chloro-1-methylpyridinium iodide (1.10 g, 4.32 mmol) and stirred for three hours at room temperature. It is diluted with 80 ml dichloromethane, washed each time twice with 50 ml 1 n hydrochloric acid, 50 ml water and once with 50 ml sodium chloride solution (saturated) and dried over magnesium sulfate. Subsequently the solvent is removed in a vacuum and the residue is purified by column chromatography (silica gel, ethyl acetate). 1.93 g PMB-CB-4-Mal (92% of theory) is obtained as a colourless oil.

EXAMPLE 8

Preparation of 3-(15-maleinimido-4,7,10,13-tetroxapentadecanoyl)cyclobutane-1,1-dicarboxylic acid (COOH-CB-4-Mal)

A solution of PMB-CB-4-Mal (1.94 g, 2.66 mmol) and anisole (4.35 ml, 39.9 mmol) in 50 ml anhydrous dichloromethane is admixed with 10 ml trifluoroacetic acid at 0° C. and stirred for two hours at 0° C. Subsequently the solvent is removed in a vacuum and the residue is purified by column chromatography (silica gel, chloroform/methanol 10:1). 1.15 g COOH-CB-4-Mal (89% of theory) is obtained as a colourless syrup.

EXAMPLE 9

Preparation of trans-(R,R/S,S)-cyclohexane-1,2-diaminoplatinum(II)-[3-(15-maleinimido-4,7,10,13-tetroxapentadecanoyl)cyclobutane-1,1-dicarboxylate](DACH-Pt-CB-4-Mal

$^1$H-NMR (D$_2$O calibrated with acetone δ=2.20 ppm): δ=0.98–1.35 (m, 4H, cyclohexyl-H), 1.44–1.62 (m, 2H, cyclohexyl-H), 1.94–2.06 (m, 2H, cyclohexyl-H), 2.28–2.48 (m, 2H, cyclohexyl-H), 2.66 (t, J=6.0 Hz, CH$_2$COO), 2.80–2.93 (m, 2H, CH$_2$CHOR), 3.34–3.50 (m, 2H, CH$_2$CHOR), 3.54–3.84 (m, 18H, NCH$_2$, OCH$_2$), 4.93 ('p', J=7.1 Hz, 1H, CHOR), 6.85 (s, 2H, C(O)CH=CHCO)

$^{13}$C-NMR (D$_2$O, calibrated with acetone): δ=24.30, 32.22 (cyclohexyl), 34.91 (CH$_2$COO), 37.37 (NCH$_2$), 38.54/38.72 (CH$_2$CHOR), 50.71 (C(COOH)$_2$), 63.05/63.09 (cyclohexyl-NH$_2$), 65.37 (CHOR), 66.52, 68.02, 69.73, 69.97, 70.01 (OCH$_2$), 134.86 (C(O)CH=CHCO), 173.39, 174.11 (C(O)CH=CHCO, CH$_2$CCOO), 180.30, 180.47 (C(COOH)$_2$)

$^{195}$Pt-NMR(D$_2$O): δ=−311

IR (KBr): ν=3448 (ss, b), 2934 (w, b), 1709 (ss), 1627 (s), 1353 (m), 1094 (ss, b), 696 (w) cm$^{-1}$

ESI-MS (4.0 kV, MeOH): m/z (%) 816.9 ([M+Na]$^+$, 100) C$_{27}$H$_{41}$N$_3$O$_{12}$Pt [794.71]

A solution of COOH-CB-4-Mal (217 mg, 445 μmol) in 5 ml water is added to an aqueous solution of [Pt trans-DACH](NO$_3$)$_2$ (175 mg, 405 μmol) which is cooled to room temperature, the latter being obtained by heating (50° C.) the platinum complex with 30 ml water. The reaction mixture is adjusted to pH 5.5 with 0.1 M KOH and stirred for three hours at room temperature in the dark. It is subsequently concentrated by evaporation in a vacuum to about 5 ml and the precipitate is centrifuged. The supernatant is purified by preparative HPLC (Nucleosil® 100-7-C18 column (250×15 mm), water/acetonitrile 80:20+0.05% TFA, flow rate: 20 ml/min, retention time: about 20 min). After removing the solvent in a vacuum and crystallizing the residue by adding about 1 ml 2-propanol, 60 mg DACH-Pt-CB-4-Mal (19% of theory) is obtained as a colourless solid.

elemental analysis: calculated: C, 40.81% H, 5.20% N, 5.29% found: C, 39.88% H, 5.16% N, 5.08%

EXAMPLE 10

Efficacy of DACH-Pt-CB-1-Mal In Vivo

Figure 1:
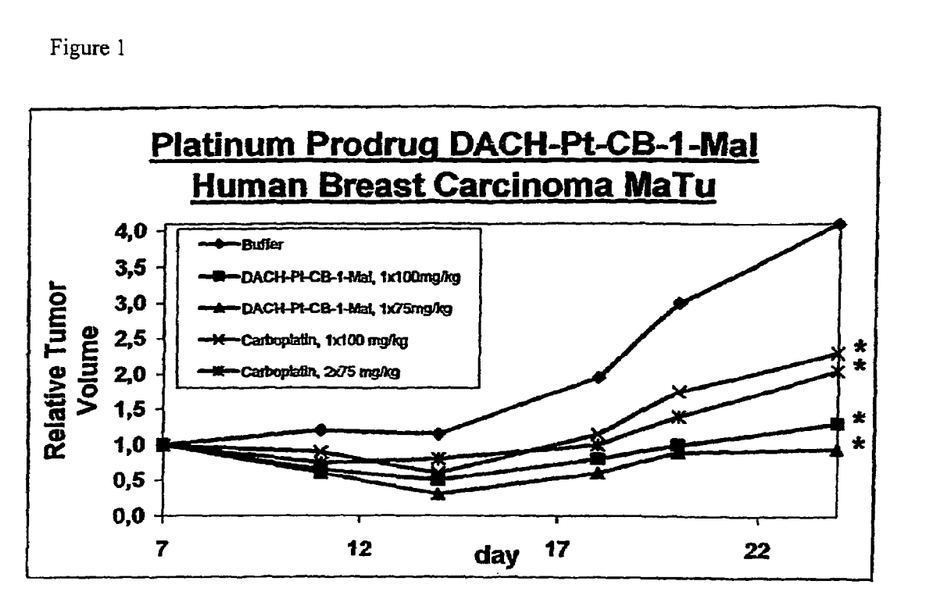

The biological data shown in FIG. 1 make it clear that the in vivo efficacy of DACH-Pt-CB-1-Mal is increased compared to carboplatin.

Animals: naked mice Tumor model: MaTu (mammary carcinoma) Treatment: DACH-Pt-CB-1-Mal (75 and 100 mg/kg) and carboplatin (100 mg/kg) once on day 7, carboplatin (75 mg/kg) on each of days 7 and 14; i.v. (carboplatin and derivatives each in 0.15 0.3 ml glucose phosphate buffer pH 6.5).

The invention claimed is:

1. Platinum complex of the general formula I:

in which R=2H,

—(CH$_2$)$_i$— (i=2 or 3);
X=O or NH; Y=O, S, or 2H;
m=0 to 5;
n=0 to 6;
PM denotes a protein-binding group.

2. Platinum complex as claimed in claim 1, characterized in that PM is a maleinimide group, a 2-dithiopyridyl group, a halogen acetamide group, a halogen acetate group, a disulfide group, an acrylic acid ester group, a monoalkylmaleic acid ester group, a monoalkylmaleaminic acid amide group, an N-hydroxysuccinimidyl ester group, an isothiocyanate group or an aziridine group which can be optionally substituted.

3. Platinum complex as claimed in claim 2, characterized in that PM is a maleinimide group which can be optionally substituted.

4. Platinum complex as claimed in claim 3, characterized in that m<2 and n=1 to 4.

5. Platinum complex as claimed in claim 4, characterized in that X=O and Y=O.

6. Process for producing platinum complexes as claimed in claim 1, characterized in that a cyclobutane-1,1-dicarboxylic acid derivative of the general formula IV in which
X=O or NH
Y=O, S or 2H
m=0 to 5
n=0 to 6
and PM denotes a protein-binding group, is reacted with a platinum complex of the general formula V in which R=2H,

—(CH$_2$)$_i$— (i=2 or 3) R'=2NO$_2$, SO$_2$ or CO.

7. Process as claimed in claim 6, characterized in that the cyclobutane-1,1-dicarboxylic acid derivative of the general formula II is obtained by reacting a 4-methoxybenzyl-protected cyclobutane-1,1-dicarboxylic acid derivative of the general formula VII in which
X=O or NH
Y=O, S or 2H
m=0 to 5
n=0 to 6
and PM denotes a protein-binding group, with trifluoroacetic acid and anisole.

8. Process as claimed in claim 7, characterized in that the cyclobutane-1,1-dicarboxylic acid derivative of the general formula VII is obtained by reacting bis(4-methoxybenzyl)-3-hydroxycyclobutane-1,1-dicarboxylate with a heterobifunctional cross-linker of the general formula VI in which
n=0, 1
m=1 to 6
and PM denotes a protein-binding group, in the presence of carboxylic acid activation reagents.

9. Process as claimed in claim 8, characterized in that N,N'-dicyclohexylcarbodiimide, N,N'-diisopropylcarbodiimide or (benzotriazole-1-yloxy)tris(dimethylamino)phosphonium hexafluoro-phosphate and most preferably 2-chloro-1-methylpyridinium iodide are used as carboxylic acid activation reagents.

10. Process as claimed in claim 8, characterized in that bis(4-methoxybenzyl)-3-hydroxycyclobutane-1,1-dicarboxylate is reacted with a maleinimidocarboxylic acid of the general formula VIa in which
n=0, 1
m=1 to 6
using 2-chloro-1-methylpyridinium iodide.

11. Process as claimed in claim 8, characterized in that bis(4-methoxybenzyl)-3-hydroxycyclobutane-1,1-dicarboxylate is obtained by reacting bis(4-methoxybenzyl)-3-tert.-butyldimethylsiloxycyclobutane-1,1-dicarboxylate with tetrabutylammonium fluoride.

12. Process as claimed in claim 11, characterized in that bis(4-methoxybenzyl)-3-tert.-butyldimethylsiloxycyclobutane-1,1-dicarboxylate is obtained by reacting bis(4-methoxybenzyl)malonate with 1,3-dibromo-2-tert.-butyldimethylsiloxypropane.

13. Pharmaceutical preparation containing a platinum complex according to claim 1 as an active ingredient, optionally together with common auxiliary substances and/or pharmaceutical solvents.

14. Process for producing a pharmaceutical preparation for treating cancer diseases, characterized in that a compound as claimed in claim 1 is transferred into a therapeutically acceptable solution.

15. A method of treating cancer comprising administering a compound of claim 1.

* * * * *